(12) United States Patent
Bandorf et al.

(10) Patent No.: US 7,867,213 B2
(45) Date of Patent: Jan. 11, 2011

(54) DISPOSABLE DIAPER IN PARTICULAR FOR INCONTINENT CARE

(75) Inventors: Matthias Bandorf, Schweinfurt (DE); Markus Benning, Gerstetten (DE); Peter Halbauer, Gerstetten (DE)

(73) Assignee: Paul Hartmann AG, Heidenheim (DE)

( * ) Notice: Subject to any disclaimer, the term of this patent is extended or adjusted under 35 U.S.C. 154(b) by 780 days.

(21) Appl. No.: 11/661,361

(22) PCT Filed: Oct. 4, 2005

(86) PCT No.: PCT/EP2005/010648

§ 371 (c)(1),
(2), (4) Date: Feb. 28, 2007

(87) PCT Pub. No.: WO2006/037595

PCT Pub. Date: Apr. 13, 2006

(65) Prior Publication Data

US 2008/0033389 A1    Feb. 7, 2008

(30) Foreign Application Priority Data

Oct. 6, 2004    (DE) .................... 10 2004 048 540

(51) Int. Cl.
A61F 13/15    (2006.01)
A61F 13/20    (2006.01)

(52) U.S. Cl. ..................... 604/394; 604/392; 604/393; 604/402

(58) Field of Classification Search ......... 604/393–396, 604/402
See application file for complete search history.

(56) References Cited

U.S. PATENT DOCUMENTS

| H1440 H | * | 5/1995 | New et al. ............. 604/386 |
| 2001/0034512 A1 | * | 10/2001 | Karlsson et al. ....... 604/392 |
| 2006/0047260 A1 | * | 3/2006 | Ashton et al. ......... 604/396 |
| 2006/0184152 A1 | * | 8/2006 | Stupperich et al. .... 604/392 |

FOREIGN PATENT DOCUMENTS

| EP | 0 464 857 | 1/1992 |
| EP | 1 142 547 | 10/2001 |
| JP | 60-181310 | 2/1985 |
| JP | 07-000453 | 1/1995 |
| JP | 2003-528695 | 9/2003 |
| WO | WO 02/22063 | 3/2002 |
| WO | WO 03/007863 | 1/2003 |
| WO | WO 03007865 A1 * | 1/2003 |

* cited by examiner

*Primary Examiner*—Melanie J Hand
(74) *Attorney, Agent, or Firm*—Paul Vincent

(57) ABSTRACT

A disposable diaper (2), in particular, for incontinent care, comprises a belt (10) having belt sections (101, 102), wherein at least one of the belt sections (101, 102) comprises a separating means (T, L) with which at least one terminal section (1011, 1021) may be separated to match the length of the belt to various hip sizes.

17 Claims, 4 Drawing Sheets

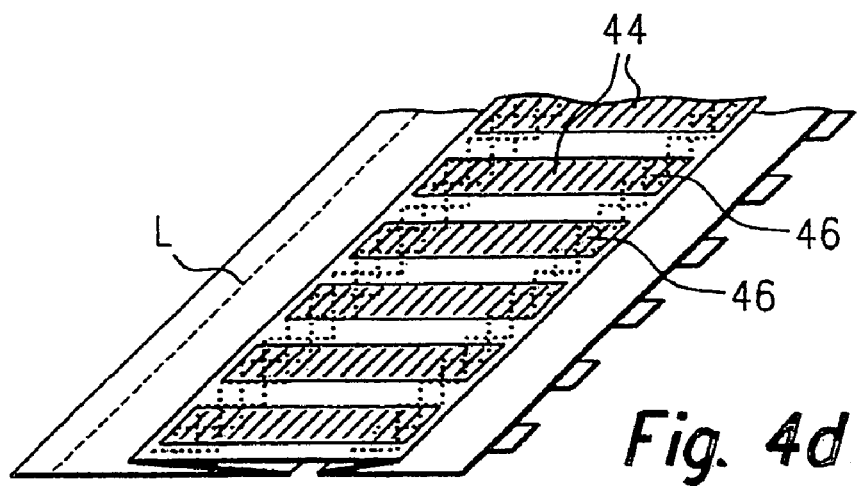
Fig. 4d
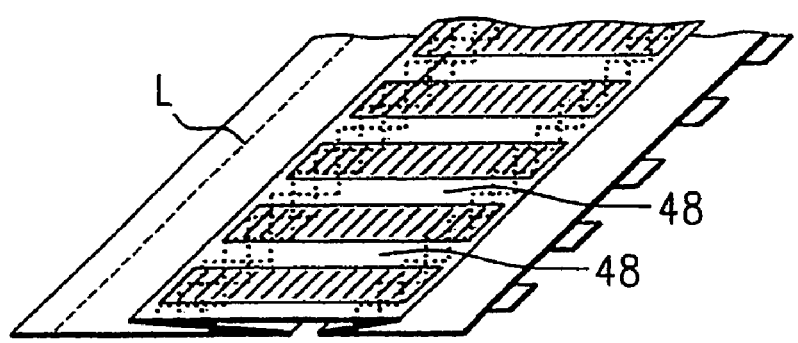
Fig. 4e

DISPOSABLE DIAPER IN PARTICULAR FOR INCONTINENT CARE

This application is the national stage of PCT/EP2005/010648 filed on Oct. 4, 2005 and also claims Paris Convention priority of DE 10 2004 048 540.2 filed on Oct. 6, 2004.

BACKGROUND OF THE INVENTION

The invention concerns a disposable diaper, in particular, for incontinent care, having a hip belt, wherein the hip belt comprises a first hip belt section with a first end section, and a second hip belt section with a second end section, wherein the first and the second hip belt sections can be fixed on top of each other using a first closing means for forming a closed hip opening, and with a diaper main part having a front area, a rear area, an intermediate crotch area and a liquid absorbing element, wherein the longitudinal end of the front area or the rear area of the diaper main part can be detachably fixed to the hip belt via second closing means, such that a user can grasp the diaper main part between his/her legs, when the hip belt has been applied, and can detachably fix the free longitudinal end of the diaper main part to the hip belt.

A disposable diaper of this type has been disclosed e.g. in US 2001/0034512 A1 or EP 1 269 949 A2.

Disposable diapers of this type are advantageous in that a user initially disposes the hip belt around the hips for applying the diaper, and can usually close it in the belly area. The diaper main part of the disposable diaper, which is usually fastened at its rear area to the belt, thereby hangs loosely downwards. After closing the hip belt, the user grasps the freely hanging end of the diaper main part and guides the diaper main part from behind and between the legs in order to fix the free longitudinal end of the diaper main part to the inside or outside of the hip belt in a detachable fashion using first closing means. It is clear that the disposable diaper may also be applied such that, after positioning and closing the hip belt, the diaper main part which hangs freely downwards, is guided from the front to the rear between the legs of a user to then be detachably mounted with its rear area to the hip belt. In other conventional disposable diapers, the diaper main part can be completely detached from the hip belt, such that the disposable diaper can be handled with great flexibility as is required, in particular, for users who require extensive care and/or are immobile.

The disposable diapers of this type are mainly used for adults. In contrast to babies and small children, the hip measurement of adults varies to a larger degree. This creates the problem of insufficient flexibility of such disposable diapers with respect to adjustment of the diaper to the hip measurement of the user.

WO-02/22063-A1 discloses a solution for this problem. It proposes to provide one of the belt halves with adhesive means, so that it can be folded. The closed hip opening is formed exclusively by the other one of the two belt halves.

This solution is disadvantageous in that on the one hand, the process of folding one of the belt halves is very difficult for the user and the folded belt half protrudes. Moreover, the folding edges produce pressure marks, in particular when the user is confined to bed.

The desired flexible length adjustment is moreover only slightly improved, since the diaper can be adjusted, in particular, to only very large and very small hip measurements.

It is the underlying purpose of the present invention to improve a disposable diaper of this type in view of the above-mentioned problem, in particular, for increasing the flexibility of length adjustment and improving handling for the user compared to conventional solutions.

SUMMARY OF THE INVENTION

This object is achieved in accordance with the invention with a disposable diaper of the above-mentioned type in that at least one of the hip belt sections has a separating means with which at least one end section can be detached for straightforward adjustment of the length of the belt to different hip measurements.

The length of at least one of the two belt sections can thereby be reduced, such that the user can adjust the hip opening formed by the closed hip belt in a very simple fashion to his/her own hip measurement.

In an advantageous embodiment of the invention, the first hip belt section, in its unfolded state, has a longer extension in the transverse direction past the longitudinal edge of the main part than the second belt section, preferably by 100 mm, preferably by 200 mm, preferentially by 300 mm, and more preferentially by 400 mm. In this case, it is advantageous that at least and preferably exclusively this first hip belt section comprises the separating means.

The first closing means are advantageously formed by an adhesive or mechanically acting element, and are disposed at the end, in particular, of the second hip belt section. With particular advantage, the first closing means are formed by a Velcro hook tape. With particular advantage, this Velcro hook tape may be brought into engagement with at least one part of the outer side of the first hip belt section for fixing the closed hip opening.

The separating means may have any design as long as one end portion of a hip belt section can be separated. In particular, weakening lines such as perforations or thin locations have proven to be advantageous. Tear strings which are known from packaging means are also suitable. In another advantageous fashion, the material forming the hip belt may be weakened by thermal treatment, in particular along a line. The separating means may simply also be formed by a small notch which facilitates tearing of the hip belt section.

In a further development of the inventive idea, one or both hip belt sections are provided with several separating means of the above-mentioned type in order to further increase the flexibility of length adjustment.

The at least one separable end section advantageously extends in the transverse direction of the diaper by at least 20 mm, preferably 30 mm-800 mm, with particular preference 50 mm-600 mm, preferentially 60 m-500 mm, and with particular preference 70 mm-400 mm and moreover, in particular, 90 mm-250 mm. It is clear that, when several separable sections are provided, these sections may have the same or a different transverse extension.

The hip belt of the inventive diaper is advantageously formed by a one-piece material section which is attached to the diaper main part in a detachable or non-detachable fashion. Due to the flat joint, no tensile forces are introduced into the main part of the diaper but can be completely accepted by the tear-resistant belt material. This offers more flexibility for selection of the chassis material forming the main part. The requirements for the stability of the joint between the belt and the main part are moreover reduced. The material section forming the belt may be obtained as one single longitudinal section of a flat material sheet supplied in the machine direction.

In a further design of the inventive idea, the hip belt is advantageously folded onto itself on both sides about folding lines that extend in the longitudinal direction of the diaper and is advantageously detachably fixed in this configuration, such that it cannot be inadvertently unfolded or opened inside the rapidly running production machine. Folding and detachable fixing of the hip belt in the folded configuration advantageously permit joining of the very long hip belt to the main part in the production machine.

In a further development of this inventive idea, the detachable fixation is advantageously formed by joints or joining areas between the folded partial sections of the material section forming the hip belt. However, the folded configuration can also be detachably fixed by other adhesive means, e.g. a detachable tape section.

The above-mentioned fixation, which can preferably be detached in one operation, of the partial sections, which are folded on top of themselves, of the material section forming the belt and joined to the main part, may e.g. be obtained through cold embossing or heated embossing (thermo welding), through needling, in particular, hot needling or through ultra sound welding or laser welding or similar joining methods having the same effect.

In the simplest case, the material section is folded on top of itself about a folding line on both sides of the longitudinal central axis, such that two partial sections are disposed on top of each other or abut each other. The material section is preferably folded on top of itself about at least two folding lines to produce a configuration with a Z-shaped cross-section. In accordance with a further preferred embodiment, the material sections are folded on top of themselves about three folding lines. In accordance with a further preferred embodiment, the material sections are folded on top of themselves about four folding lines.

In accordance with a further preferred embodiment of the inventive belt diaper, in the folded configuration, the hip belt, in particular the one-piece material section of the hip belt, projects with a grasping area past a longitudinal side edge of the diaper main part. The grasping area may be formed, in particular, by the respective free end of the hip belt.

Before unfolding the one-piece material section, the grasping areas advantageously face to the outside in the transverse direction, i.e. face away from each other and from a longitudinal central axis of the diaper main part disposed on a flat support, such that a user can grasp them conveniently with the left hand from the left side and with the right hand from the right side. The belt diaper is particularly advantageous for persons who need a great deal of care. The belt diaper is e.g. often applied to patients in need of care, while they are lying on their sides. The material section that laterally projects past the main part must thereby be guided beneath the patient. This process of guiding underneath the patient is substantially simplified with the detachably fixed, folded material section that forms the belt.

The detachable fixation of the material section partial sections, which are folded on top of each other, to each other and possibly also to the main part is preferably effected by several point-shaped joints. A point-shaped joint of the above-mentioned type means that the joint has an area (projected onto the X-Y plane of the main part) of less than 5 mm$^2$, in particular, less than 2 mm$^2$ and moreover, in particular, less than 1 mm$^2$. The joints need not be strictly point-shaped or circular. Shapes other than point-shaped or circular, e.g. triangular, rectangular, polygonal or oval shapes are also feasible and advantageous. The detachable fixation of the material section partial sections, which are folded on top of each other, to each other is realized through preferably point-shaped joints which are generated by heat or ultrasound.

The material section forming the hip belt extends in the unfolded state in the transverse direction beyond the longitudinal edge of the main part by at least 200 mm, in particular at least 300 mm, in particular at least 400 mm, in particular at least 500 mm, and moreover in particular at least 600 mm, and in particular at least 700 mm, and preferentially at least 800 mm.

It extends in the longitudinal direction by 30 to 120 mm, in particular 30 to 100 mm, in particular 30 to 80 mm, in particular 30 to 75 mm, in particular 44 to 70 mm, in particular 40 to 65 mm and moreover, in particular 40 to 60 mm.

The one-piece material section is advantageously undetachably joined to an outer side of the main part. It may be joined by any means. The one-piece material section may thereby be advantageously joined to the diaper main part using an adhesive which is applied only in areas. With particular preference, the adhesive is not provided up to the edge of the mutually abutting flat extension of the material section and the main part, such that a peripheral edge area of this bond remains without adhesive. This is advantageous in that in this case, no adhesive is forced from between the layers to the outside during lamination.

The present invention also concerns a method for producing a disposable diaper of the above-mentioned type. This method is characterized by the following steps:

supplying an endless flat material sheet for forming material sections for producing the hip belt;

folding the flat material sheet about folding lines that extend in the longitudinal direction, wherein the flat material sheet is folded on top of itself on both sides of a longitudinal central axis;

separating the longitudinal sections of the folded flat material sheet for forming in each case a one-piece material section for producing the hip belt; and detachably fixing the material section to a diaper main part.

Preferred further developments of the inventive method can be extracted from the dependent method claims. With particular preference, the one-piece material section forming the hip belt is joined to the diaper main part using an adhesive. The adhesive is thereby moreover advantageously disposed on longitudinally spaced-apart areas of the flat material sheet from which the material sections are separated. A respective cut region is thereby preferably left without glue.

It is also advantageous to dispose the glue onto areas of the flat material sheet such that it is separated, in the longitudinal direction and preferably also in the transverse direction, from an edge of flat material sections which are later separated. In this case, it is advantageous to dispose the glue in cycles onto the flat material sheet.

The one-piece material section joined to the main part is preferably formed from a non-woven material, in particular and preferably by using spunbond materials (S) or spunbond-meltblown materials (SM), or meltblown layers (SMS) which are provided on both sides with spunbond materials or also carded non-woven materials. Non-woven laminates, i.e. in particular, two-layered, three-layered or multi-layered combinations of the above-mentioned non-woven materials may also be used. The individual layers may e.g. be connected by conventional and familiar methods, e.g. through thermal joining methods (welding, in particular laser welding, hot melt, air-through) or through ultrasound welding methods. Cold pressing, needling, sewing or gluing of non-woven materials is also feasible. Connecting to textile tissues, knitted fabrics, i.e. to materials having a textile bond in the broadest sense is also feasible. Films of thermoplastic and, in particular, elastic materials may also be used, also in the form of multi-layered film laminates. Non-woven/sheet laminates may advantageously also be used, which comprise at least one film layer and at least one non-woven layer or at least one layer of a textile material. Film layers are used, in particular, to realize elastic areas of the belt. The connection of the layers may, in turn, be realized by the above-mentioned methods.

The material section is advantageously designed to be breathable at least in sections, wherein, in particular, microporosity is regarded as being advantageous, which permits air exchange and also permeability for moisture in the form of water vapor. The material sections advantageously have a surface density of 20 to 150 g/m$^2$, in particular 30 to 100 g/m$^2$ and preferentially 40 to 80 g/m$^2$.

BRIEF DESCRIPTION OF THE DRAWING

Further features, details and advantages of the invention can be extracted from the enclosed claims and the drawing and following description of a preferred embodiment of the inventive diaper.

FIGS. 4a-e schematically show the supply, folding, fixing, adhesive coating and cutting of a flat material sheet forming hip belt sections.

DESCRIPTION OF THE PREFERRED EMBODIMENT

Figure 1:
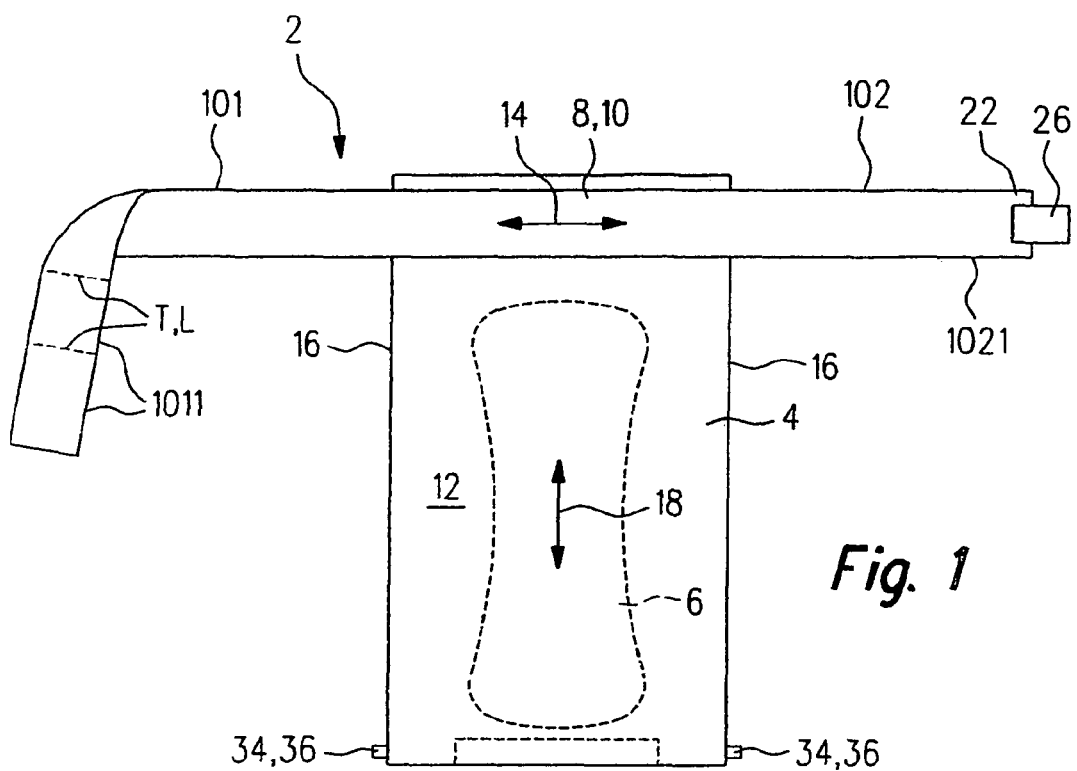
FIG. 1 shows a schematic view of an inventive belt diaper with unfolded hip belt.
Figure 2:
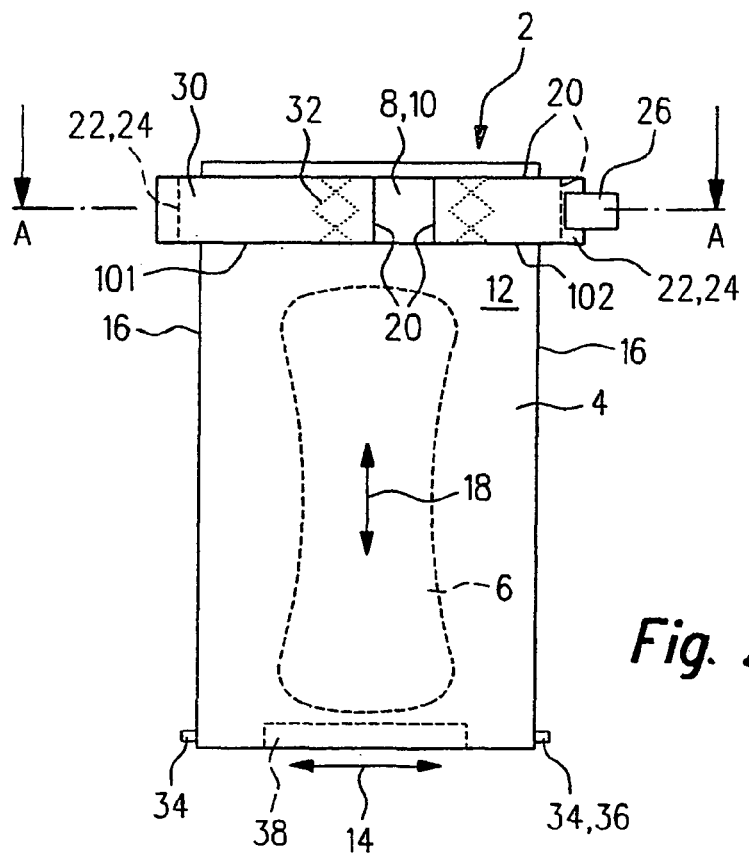
FIG. 2 shows a schematic view of an inventive belt diaper with folded hip belt.

FIGS. 1 and 2 schematically show a disposable belt diaper 2 with a main part 4 and an indicated absorbing element 6. A one-piece material section 8 is joined to the main part 4 to form a hip belt 10 of the belt diaper. FIG. 1 shows the belt in the unfolded state, and FIG. 2 shows the belt in the folded state. FIG. 1 shows two spaced-apart separating means T in the form of perforation lines L at a first hip belt section 101 that projects past the side edge of the main part 4. The one-piece material section 8 is undetachably joined to an outer side 12 of the main part 4 in a manner described in detail below. It extends, in the unfolded state, in the transverse direction 14 of the belt diaper 2 past lateral longitudinal edges 16 in each case by at least 300 mm, in particular at least 400 mm, in particular at least 500 mm, in particular at least 600 mm. In the case illustrated in FIG. 1, the first material section 101 is clearly longer than the second material section 102, i.e. the transverse extension 14 of the first hip belt section 101 in the unfolded state past the longitudinal edge 16 of the main part 4 is larger than that of the second hip belt section 102, preferably by 100 mm, with particular preference by 200 mm, and preferentially by 300 mm.

In FIG. 2, the one-piece material section 8 is folded several times on top of itself about folding lines 20 on both sides in the longitudinal direction of the diaper 18. The respective free end 22 of the material section 8 forms a grasping area 24 which projects by at least 10 mm past the longitudinal side edges 16, which the user grasps with his/her fingers. A closing element 26 is also provided at the end 22 of the first hip belt section 102, e.g. in the form of a tab which is adhesive or preferably comprises mechanically acting closing elements, and can cooperate in a detachable adhesive fashion with an engagement area or matching closing element at the first hip belt section 101, in particular, with its entire outer surface when the hip belt 10 is closed to form a hip opening that is closed in the peripheral direction of the hip. The outer side of the hip belt advantageously comprises a fiber material, such as e.g. a textile or a non-woven material that can be brought into direct engagement with the closing element 26.

The partial sections 30 of the one-piece material section 8, which are folded on top of each other, are detachably fixed on top of each other by a number of substantially point-shaped joints 32 in the form of preferably ultrasound welding points. A few joints are sufficient therefor.

The hip belt 10 is unfolded for applying the belt diaper 2. In order to adjust the length, an end section 1011 of the first hip belt section 101 may subsequently be separated either along the first or the second perforation line L.

The hip belt is then closed on top of itself via the closing element 26 of the second hip belt section 102 and the correspondingly designed engagement area on the first hip belt section 101. The user or the nursing staff then takes the end of the main part that usually hangs freely downwards from between the legs of the user and fastens it in a detachable fashion to the annularly closed hip belt 10, preferably on the outer side of the hip belt 10 facing away from the user. The main part 4 may, in turn, be detachably fixed via any closing means 34, which are per se adhesive or mechanically acting, in the present case via closing tabs 36 that laterally project past the main part. A corresponding covering area 38, preferably on the inner side of the main part 4 facing the body, may additionally be provided with closing means in the widest sense and of any design per se.

Figure 3:
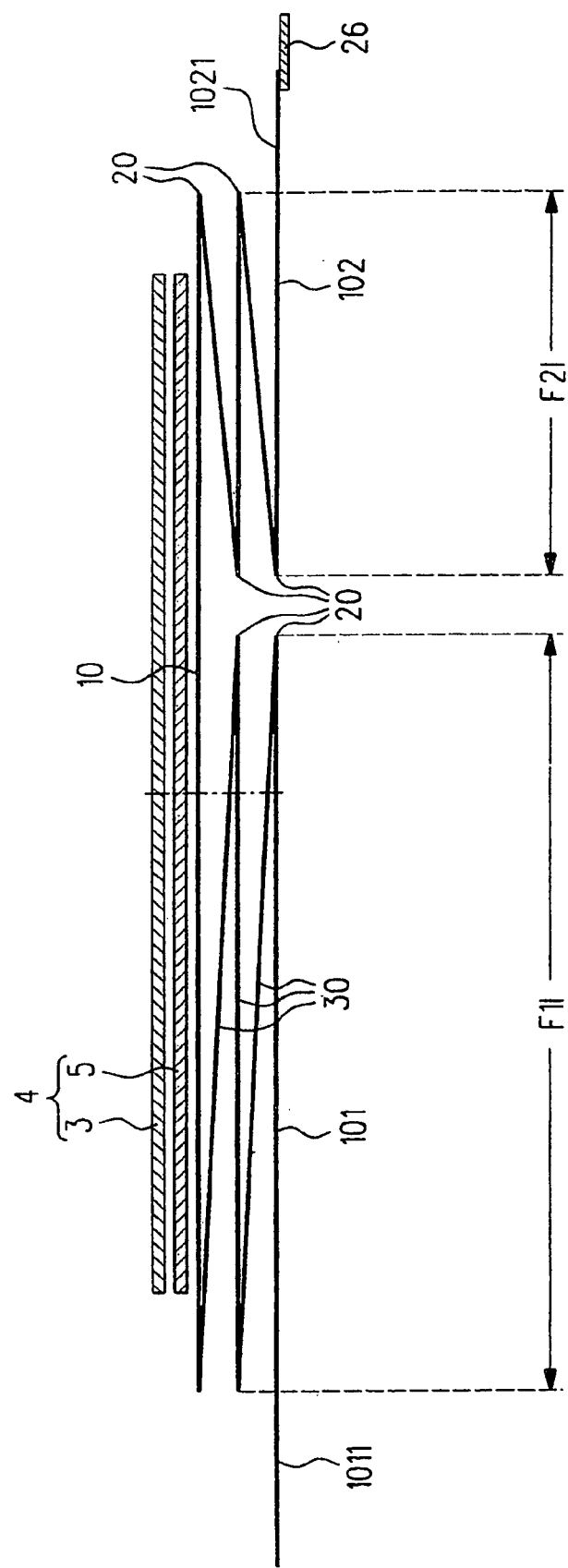
FIG. 3 shows a schematic sectional view, with sectional plane A-A, of the belt of FIG. 2 with a first fold of the hip belt.

FIG. 3 shows a particularly preferred folding of the one-piece material section 8 which is mounted at the outside, i.e. facing away from the body, to the end of the diaper main part 4. In this example, the diaper main part is formed at its end by a top sheet 3 on the side of the body and a back sheet 5 on the side of the clothes. The folding comprises four folding lines 20 on each side. Each folding is thus double z-shaped. The belt is asymmetrically folded. The fold width (F1, 1) of the first longer hip belt section 101 is larger than the fold width (F2, 1) of the shorter, second hip belt section 102.

The overall length of the hip belt 10 (including the transverse extension over the main part, i.e. the peripheral length of the entire hip opening) is approximately 1400 mm (any area that overlaps when the hip belt 10 is closed, is not taken into consideration). The belt width, i.e. its extension in the longitudinal direction 18 is between 50 and 100 mm.

Figure 4A:
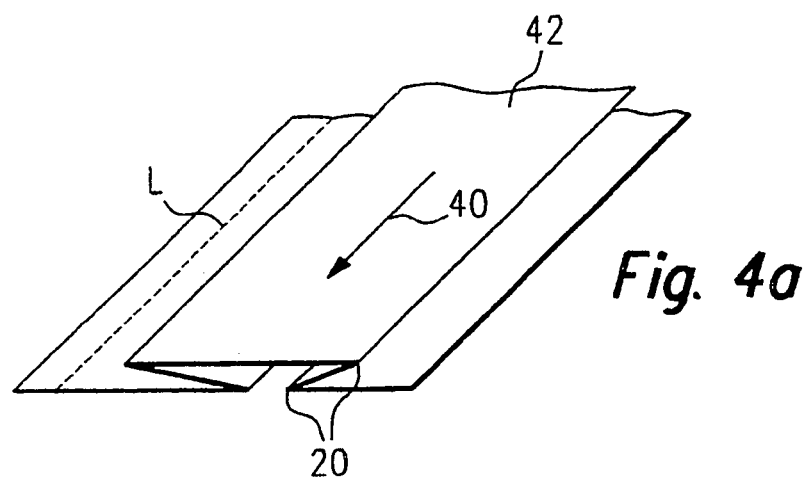
Figure 4B:
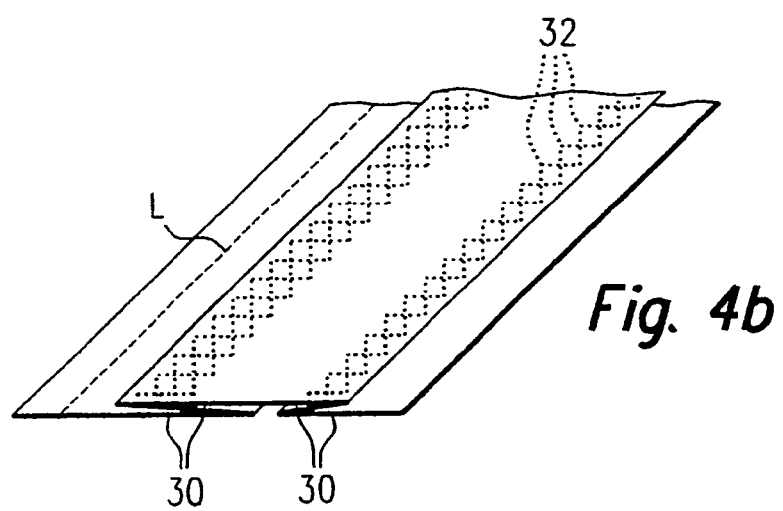
Figure 4C:
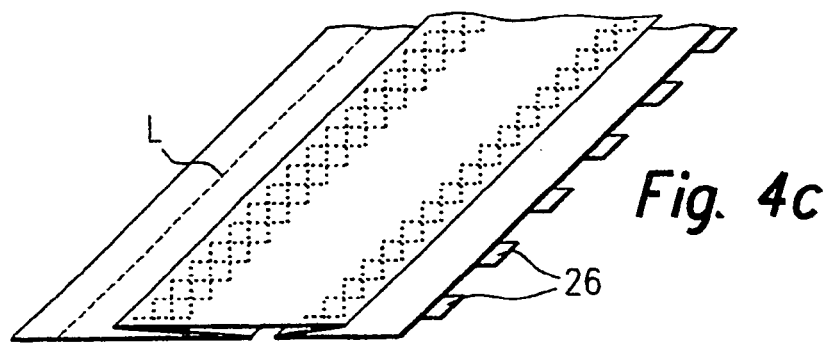

FIGS. 4a to 4e show the production method of an inventive belt diaper, i.e. the production of the hip belt 10. Towards this end, an endless flat material sheet 42 is supplied in a longitudinal direction 40 of the machine. The flat material sheet already has a perforation line L. It is clear that the belt material may also be provided with the separating means at a later time. In the presented case of FIG. 4a, the flat material sheet 42 is folded, as an example, about two folding lines 20, i.e. in a Z-shape. Folding about three or four or more folding lines is also feasible. The partial sections 30 folded on top of each other are detachably fixed to each other as is schematically shown in FIG. 4b. This may be advantageously realized by substantially point-shaped joints 32, in particular, by ultrasound welding points. FIG. 4c shows the joining of closing elements 26 to a side of the folded flat material sheet 42.

Glue 44 is then disposed in some areas 46 of the flat material sheet 42, which are spaced apart in the longitudinal direction 40, preferably in a cycled method (see FIG. 4d).

Longitudinal sections 47 are then separated from the endless flat material sheet 42 transversely to the longitudinal direction 40 (FIG. 4e), which represent the material section 8 which is continuous in one piece in the transverse direction to form the hip belt 10. FIG. 4e shows that the cut is made in areas 48 without glue.

The separated longitudinal section 47 of the flat material sheet 42 is then advantageously permanently attached to the outer side 12 of a diaper main part 4, as is shown in FIG. 1 and described above.

We claim:

1. A disposable diaper suitable for incontinence care, the diaper comprising:
    a first hip belt section having a first end section;
    a second hip belt section having a second end section;
    a first closing means disposed on one of said first and said second end sections, said first and second hip belt sections being fixed on top of each other using said first closing means to form a hip belt having a closed hip opening;
    a diaper main part having a front area, a rear area, an intermediate crotch area, and a liquid absorbing element;
    second closing means for detachably fixing a longitudinal end of said front area or said rear area of the diaper main part to said hip belt such that a user can grasp said diaper main part from between his/her legs, when said hip belt is applied, to detachably fix a free longitudinal end of said diaper main part to said hip belt; and
    separating means disposed on at least one of said first and said second hip belt sections for separating at least one of said first and said second end sections to shorten a length of said hip belt for different hip sizes, wherein, in an unfolded state, at least one of said first and said second hip belt sections extends in a transverse direction past a longitudinal edge of said main part by at least 200 mm, 300 mm, 400 mm, 500 mm, 600 mm, 700 mm, or 800 mm.

2. The disposable diaper of claim 1, wherein a transverse extension of said first hip belt section, in an unfolded state, past a longitudinal edge of said main part is larger than that of said second hip belt section by 100 mm, 200 mm, 300 mm, or 400 mm.

3. The disposable diaper of claim 1, wherein at least one of said first and said second the hip belt sections comprises at least two three or four said separating means for separating several end sections or end sections of different lengths.

4. The disposable diaper of claim 1, wherein said separating means is/are formed by a weakening line or a perforation line having a component in a longitudinal direction of the diaper.

5. The disposable diaper of claim 1, wherein at least one of said first and said second end section which is structured for separation extends in a transverse direction of the diaper by at least 20 mm, 30 mm-800 mm, 50 mm-600 mm, 60 mm-500 mm, 70 mm-400 mm, 80 mm-300 mm, or 90 mm-200 mm.

6. The disposable diaper of claim 3, wherein end sections that are separable have different extensions in a transverse direction of the diaper.

7. The disposable diaper of claim 1, wherein said hip belt is folded onto itself on both sides about folding lines that extend in a longitudinal direction of the diaper.

8. The disposable diaper of claim 7, wherein a folding width of said first hip belt section is larger than a folding width of said second hip belt section.

9. The disposable diaper of claim 7, wherein said hip belt is detachably fixed in a folded configuration.

10. The disposable diaper of claim 9, wherein a detachable fixing is formed by joints or joining areas between partial sections of said hip belt, which are folded on top of each other.

11. The disposable diaper of claim 10, wherein said joints or joining areas are substantially point-shaped.

12. The disposable diaper of claim 1, wherein said hip belt is folded onto itself on both sides about three or four folding lines which each extend in a longitudinal direction of the diaper.

13. The disposable diaper of claim 1, wherein, in a folded configuration, a grasping area of said hip belt projects in a transverse direction past a longitudinal side edge of the diaper main part.

14. A disposable diaper suitable for incontinence care, the diaper comprising:
    a first hip belt section having a first end section;
    a second hip belt section having a second end section;
    a first closing means disposed on one of said first and said second end sections, said first and second hip belt sections being fixed on top of each other using said first closing means to form a hip belt having a closed hip opening;
    a diaper main part having a front area, a rear area, an intermediate crotch area, and a liquid absorbing element;
    second closing means for detachably fixing a longitudinal end of said front area or said rear area of the diaper main part to said hip belt such that a user can grasp said diaper main part from between his/her legs, when said hip belt is applied, to detachably fix a free longitudinal end of said diaper main part to said hip belt; and
    separating means disposed on at least one of said first and said second hip belt sections for separating at least one of said first and said second end sections to shorten a length of said hip belt for different hip sizes, wherein said hip belt extends in a longitudinal direction by 30 to 120 mm, 30 to 100 mm, 30 to 80 mm, 30 to 75 mm, 44 to 70 mm, 40 to 65 mm, or 40 to 60 mm.

15. The disposable diaper of claim 1, wherein said hip belt is formed by a one-piece material section.

16. A disposable diaper suitable for incontinence care, the diaper comprising:
    a first hip belt section having a first end section;
    a second hip belt section having a second end section;
    a first closing means disposed on one of said first and said second end sections, said first and second hip belt sections being fixed on top of each other using said first closing means to form a hip belt having a closed hip opening;
    a diaper main part having a front area, a rear area, an intermediate crotch area, and a liquid absorbing element;
    second closing means for detachably fixing a longitudinal end of said front area or said rear area of the diaper main part to said hip belt such that a user can grasp said diaper main part from between his/her legs, when said hip belt is applied, to detachably fix a free longitudinal end of said diaper main part to said hip belt; and
    separating means disposed on at least one of said first and said second hip belt sections for separating at least one of said first and said second end sections to shorten a length of said hip belt for different hip sizes, wherein said hip belt is undetachably joined to an outer side of said main part.

17. The disposable diaper of claim 15, wherein said one-piece material section is joined to said diaper main part using an adhesive which is disposed thereon or disposed only in certain areas thereon.

* * * * *